United States Patent [19]

Berndt

[11] Patent Number: 5,770,394
[45] Date of Patent: Jun. 23, 1998

[54] METHOD AND APPARATUS FOR DETECTING BACTERIA USING A BLOOD CULTURE FROTH

[75] Inventor: Klaus W. Berndt, Stewartstown, Pa.

[73] Assignee: Becton Dickinson and Company, Franklin Lakes, N.J.

[21] Appl. No.: 651,313

[22] Filed: May 22, 1996

[51] Int. Cl.$^6$ .............................. C12Q 1/04; C12M 1/34
[52] U.S. Cl. .................... 435/34; 435/287.5; 435/288.1; 435/288.7; 435/808
[58] Field of Search .................................. 435/4, 29, 30, 435/34, 287.1, 287.5, 288.1, 288.7, 808, 304.1

[56] References Cited

U.S. PATENT DOCUMENTS 3,566,114  2/1971  Brewer ................................ 435/288.7
4,293,643  10/1981 Ohtake et al. ........................ 435/288.7
4,940,332  7/1990  Miwa et al. .......................... 435/288.7
5,510,620  4/1996  Achter et al. ....................... 250/339.12

OTHER PUBLICATIONS

WPIDS Abstract 89–000645 of Graf. German Patent DE 3735824 (Oct. 1988).

Primary Examiner—William H. Beisner
Attorney, Agent, or Firm—Alan W. Fiedler

[57] ABSTRACT

The present invention describes a method and apparatus for detecting bacteria in blood culture bottles with a chemical sensor dissolved directly in the culture medium that (1) introduce a blood specimen, a growth medium, and a soluble chemical sensor dye into a sealable container, (2) agitate the container vigorously so that a froth is generated above the liquid, and (3) monitor the spectroscopic characteristics of the blood culture froth. The spectroscopic characteristics are then analyzed to determine whether bacteria are present in the blood culture bottle.

6 Claims, 7 Drawing Sheets

METHOD AND APPARATUS FOR DETECTING BACTERIA USING A BLOOD CULTURE FROTH

BACKGROUND OF THE INVENTION

1. Field of the Invention

The present invention relates to a method and apparatus for detecting bacteria in blood culture bottles and for differentiating between organism species using a blood culture froth.

2. Background Description

The presence of biologically active agents such as bacteria in a patient's body fluid, especially blood, is generally determined using blood culture bottles. A small quantity of blood, typically 1 to 10 ml, is injected through an enclosing rubber septum into a sterile bottle containing a culture medium, and the vial is then incubated at 37° C. and monitored for bacterial growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different vials. It has also been proposed to detect microorganism growth in sealable containers by monitoring positive and/or negative pressure changes.

Recently, non-invasive methods have been developed involving chemical sensors disposed inside the vial. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each vial. This results in station sensitivity variations from one vial to the next. Additional problems are caused by the aging effects of the light sources, filters and photodetectors. Due to the fact that most known blood culture sensors generate only a moderate contrast ratio in the measured photocurrent during bacterial growth, extensive and time-consuming calibration procedures and sophisticated detection algorithms are required to operate these systems. In addition, flexible electrical cables are required to connect the individual sources and detectors with the rest of the instrument. With the large number of light sources, typically 240 or more per instrument, maintenance can become very cumbersome and expensive when individual sources start to fail.

When chemical sensors are disposed to the inner bottom of blood culture bottles, the active fluorometric or calorimetric dye is usually embedded in a matrix material such as silicone rubber. The sensor mixture is, therefore, injected into the bottle and has to be cured under specific conditions regarding humidity and temperature. Since the curing process can extend over a few days, production cost is increased.

Standard blood culture bottles exhibit irregularities in the shape of their bottom. In most cases, the bottom shows a convex curvature, and the bottom may be slightly tilted. It is therefore necessary to inject a relatively large amount of sensor material into each bottle in order to cover the whole bottom surface. This results in an increased sensor thickness and increases the cost further due to the extreme high dye prices.

It has also been found that an increased sensor thickness causes an increase in the sensor's response time in regard to analyte changes, since the analyte is being diffused into the sensor matrix at a limited speed. If the sensor is thicker, it takes a longer time for the diffusion process. In other words, a thick sensor matrix can cause a delay of several hours in the time required to detect the presence of bacteria.

If one would dissolve a chemical sensor material directly in the culture medium, the active dye would be in direct contact with the analyte. Consequently, no delay in the sensor's response would be expected. Dissolving the dye in the culture medium would also eliminate the complex process of disposing material at the bottom, and eliminate the need for the curing process, which would reduce cost. Unfortunately, the high optical absorption of the blood makes it impossible to apply this principle. In one known blood culture system, a fluorescent dye is dissolved in the culture medium. However, in order to perform a bottle reading, one has to wait approximately two hours until the blood cells have settled down. During this waiting time, the blood culture bottle can not be agitated as usual. Agitation is required, however, to allow for optimum bacterial growth. Non-optimum agitation results in a delay in the time to detection. Also, if a bottle is removed from the blood culture system for visual inspection, an additional waiting time of two hours is required until a next reading can be executed.

In view of these problems, there still exists a need for a practical method to read a chemical sensor that is dissolved directly in the blood culture medium.

SUMMARY OF THE INVENTION

It is an objective of the present invention to overcome the above problems of the prior art by providing a method and apparatus for detecting bacteria in blood culture bottles with a chemical sensor dissolved directly in the culture medium.

According to the present invention, the above objective is achieved by (1) introducing a blood specimen, a growth medium, and a soluble chemical sensor dye into a sealable container, (2) agitating the container vigorously so that a froth is generated above the liquid, and (3) monitoring the spectroscopic characteristics of the blood culture froth.

These and other aspects, features and advantages of the present invention will become apparent from the following detailed description, taken in conjunction with the accompanying drawings.

DETAILED DESCRIPTION

According to the present invention, blood, a growth medium, and a soluble chemical sensor dye are introduced into a sealable container. The container is agitated vigorously so that a froth is generated above the liquid mixture. Then, spectroscopic characteristics of the blood culture froth are investigated in order to make a decision regarding the presence of bacteria.

Figure 1:
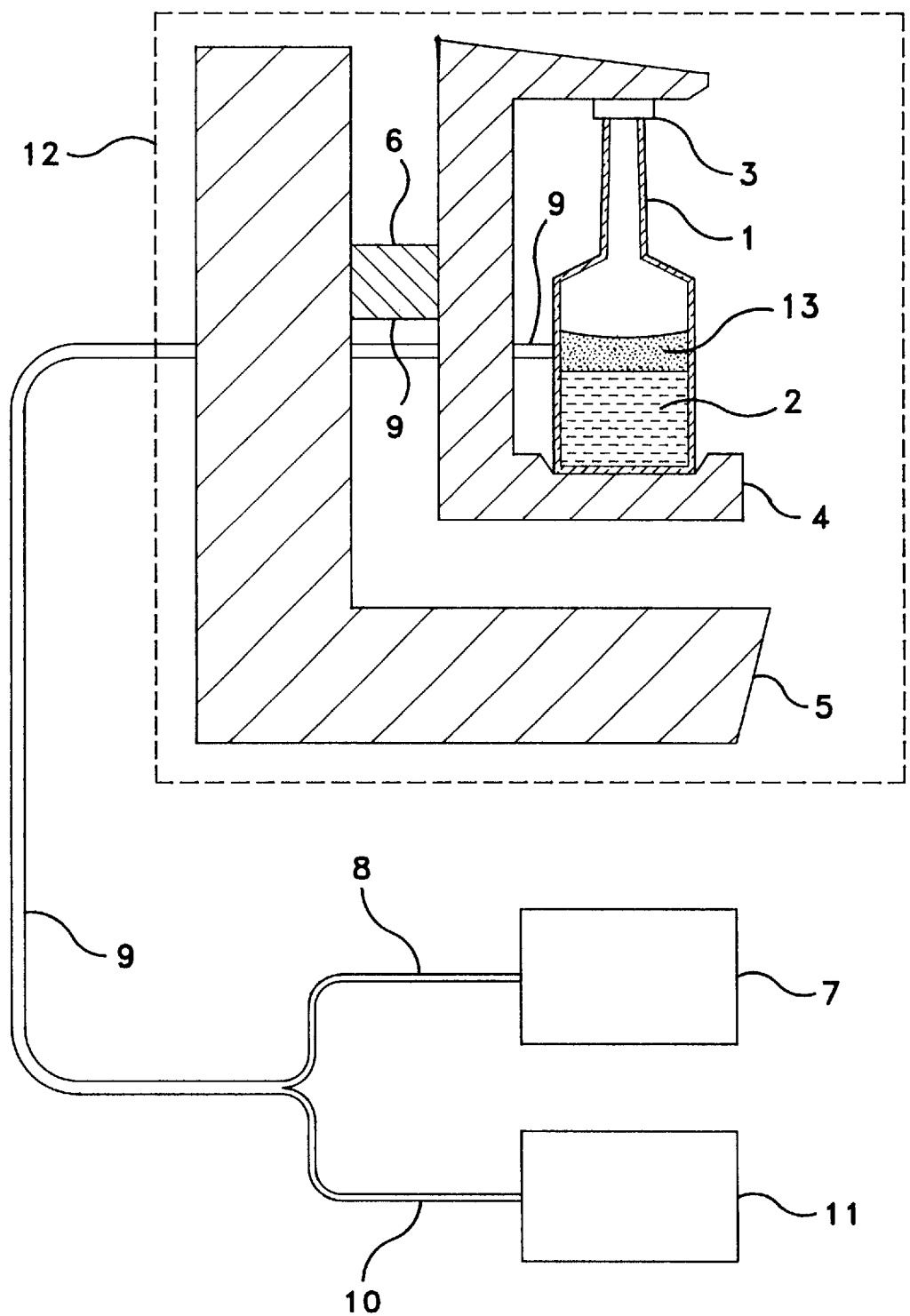
FIG. 1 is a schematic drawing of an apparatus for detecting bacteria according to the present invention.

An apparatus embodying the principles and concepts of the invention is illustrated schematically in FIG. 1. A blood culture bottle 1 containing a liquid mixture 2 of blood, a conventional culture media, and a soluble fluorescent chemical sensor dye (discussed below), and having a closure cap 3, is arranged in a holder 4. Holder 4 is connected by a block 6 to an agitator 5, which shakes holder 4 and blood culture bottle 1 vigorously so that a blood culture froth 13 is generated above liquid mixture 2. A wavelength-tunable narrow-band light source 7 is connected to one branch 8 of a bifurcated fiber bundle 9. The other branch 10 of bundle 9 is coupled to a light detector 11. Bundle 9 is connected to agitator 5 and holder 4 in such a way that its common end is located outside of bottle 1 adjacent froth 13. Agitator 5 holding bottle 1 is mounted inside a light tight housing 12.

During operation, agitator 5 shakes bottle 1 until a dense blood culture froth has been generated. This happens within a time interval of one to five seconds. It has been found that a blood culture froth is stable over an extended time interval, at least over half an hour, which provides more than enough time for measuring spectroscopic characteristics of the blood culture froth 13.

Figure 2:
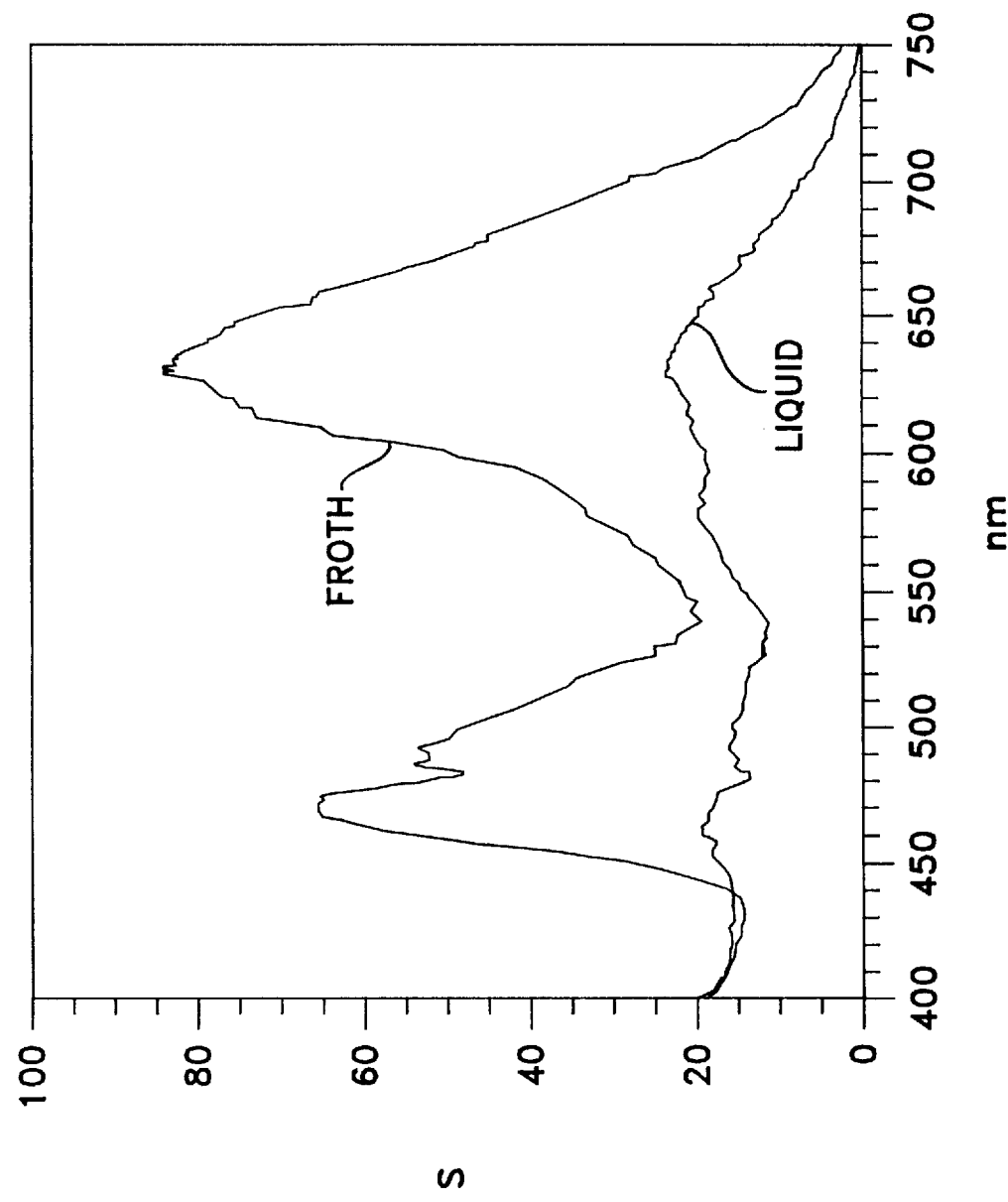
FIG. 2 shows a plot depicting back-scattering spectra measured on a liquid blood/media mixture and on a blood culture froth above the liquid.

The invention can be applied in various ways. First, we will describe an application that does not even require the addition of a fluorescent dye to the blood/media mixture. If one measures a so-called back-scattering spectrum of froth 13, one obtains a spectrum similar to the one shown in FIG. 2, which consists of two distinct maxima. FIG. 2 also shows a back-scattering spectrum of the liquid blood/media mixture. As can be seen, the froth spectrum has a significantly higher intensity. This is an important advantage, because for the froth, glass-reflex artifacts from the bottle walls are much less severe than in the case where one measures the spectrum of the liquid.

Figure 3:
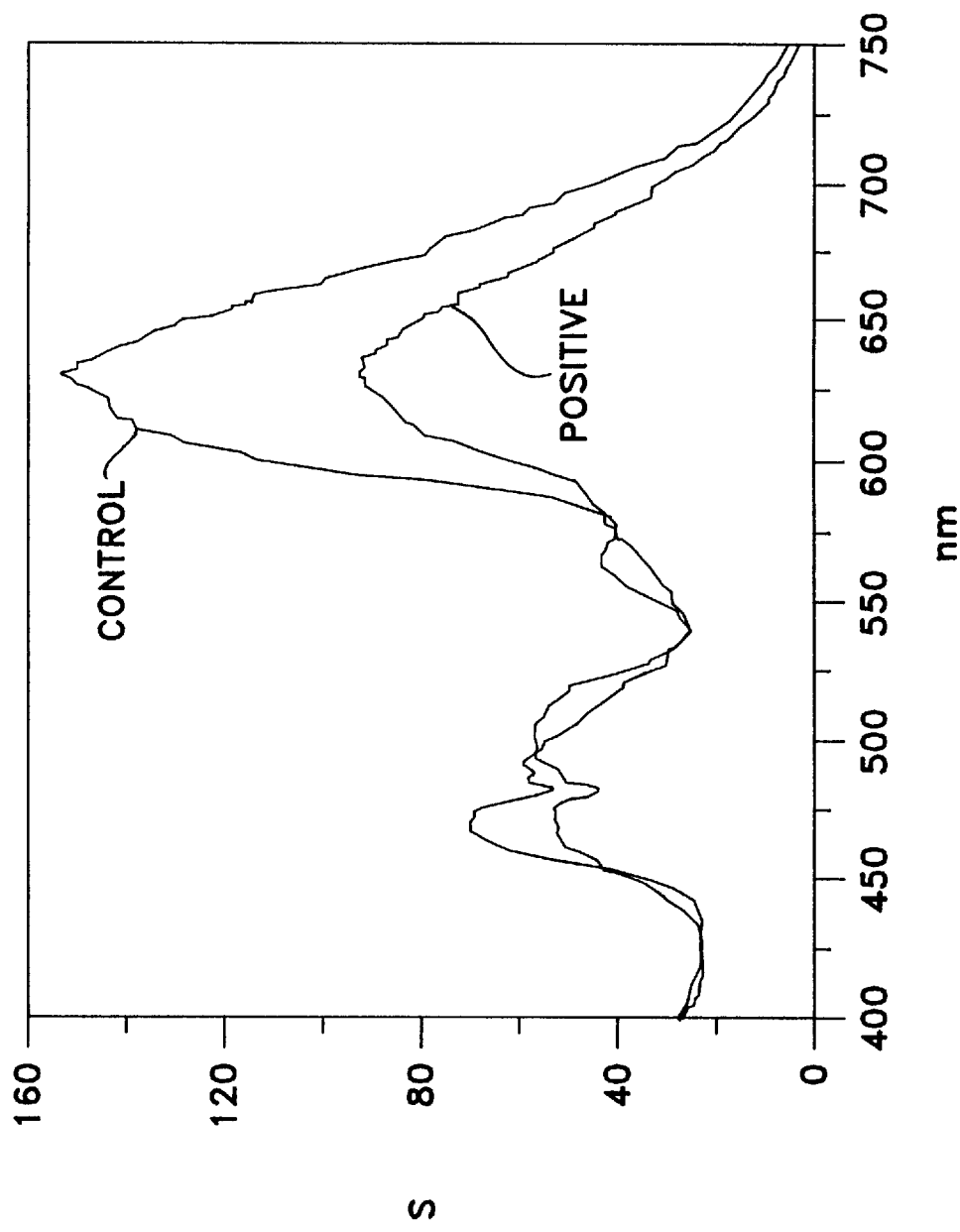
FIG. 3 shows a plot depicting the back-scattering spectra measured on a blood culture froth for a bottle with no bacteria and for a bottle containing bacteria (positive)
Figure 4:
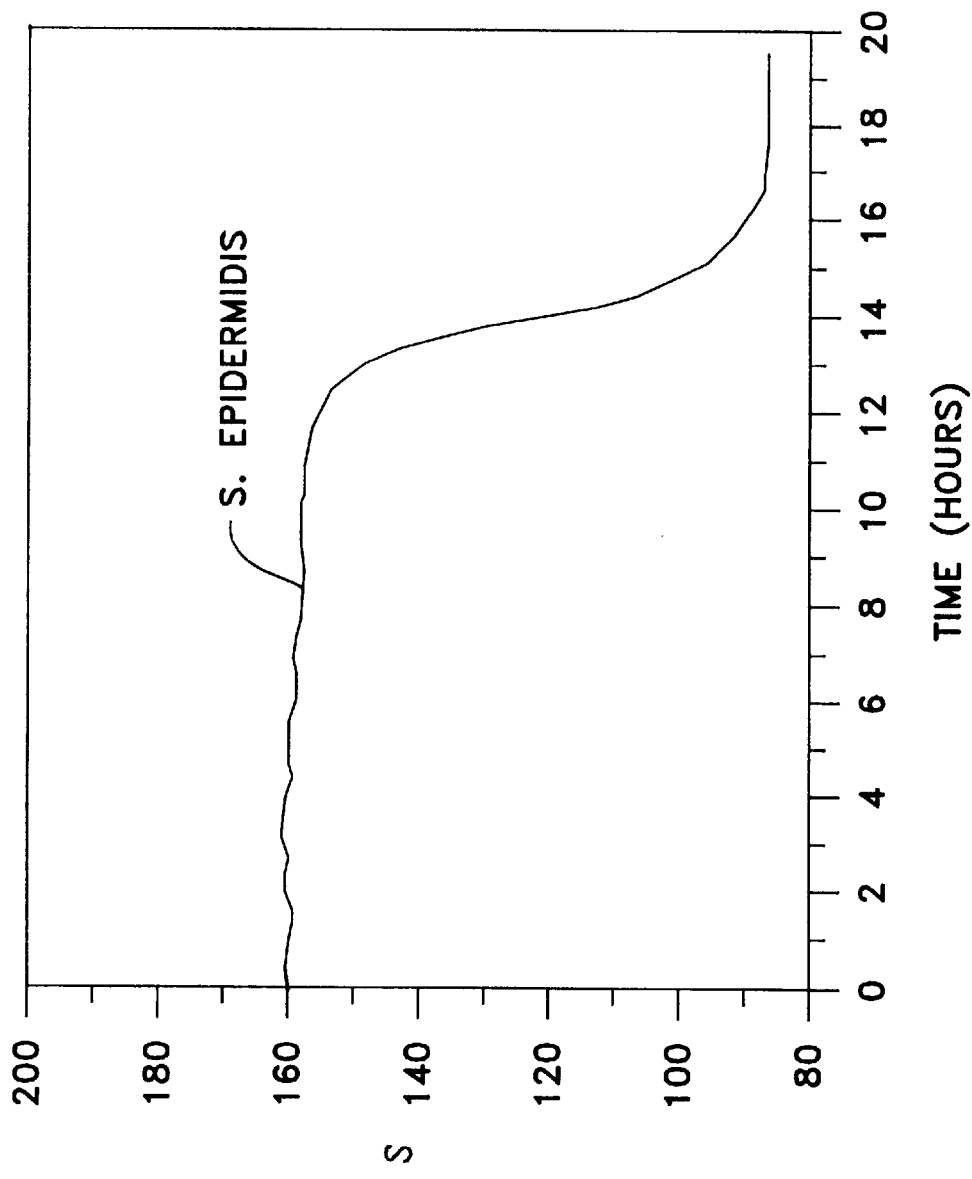
FIG. 4 shows a plot depicting the back-scattering intensity at 630 nm versus time as a bottle containing S. epidermidis becomes positive.

FIG. 3 depicts two back-scattering spectra, measured on blood culture froth 13 for a bottle with no bacteria (control) and for a bottle containing bacteria (positive). The two spectra exhibit a serial of characterization differences that allow one to make an immediate decision if a bottle contains bacteria or not. For a positive bottle the peak at 630 nm is lower than in the case of a control bottle. Also, the small peak at 560 nm present in the control bottle disappears in positive bottles. Furthermore, the difference between the peak heights at 465 nm and 490 nm is negative for a negative bottle, and positive for a positive bottle. FIG. 4 is a plot showing the back-scattering intensity at 630 nm versus time, as a bottle containing S. epidermidis becomes positive. As can be seen from this FIG. 4, the curve contains a sharp decrease 12 to 15 hours after inoculation, which is the typical time to detection for S. epidermidis as observed using known blood culture systems. Therefore, a blood culture froth without an added dye can be used to distinguish between positive and negative bottles and/or to monitor a growing microorganism population over time. It would be within the spirit of the invention either to register whole spectra as shown in FIGS. 2 to 3, or to select specific spectral windows using band-pass, short-pass, and/or long-pass filters. It would also be within the spirit of the invention to apply ratiometric principles or to apply other data analysis tools.

Figure 5:
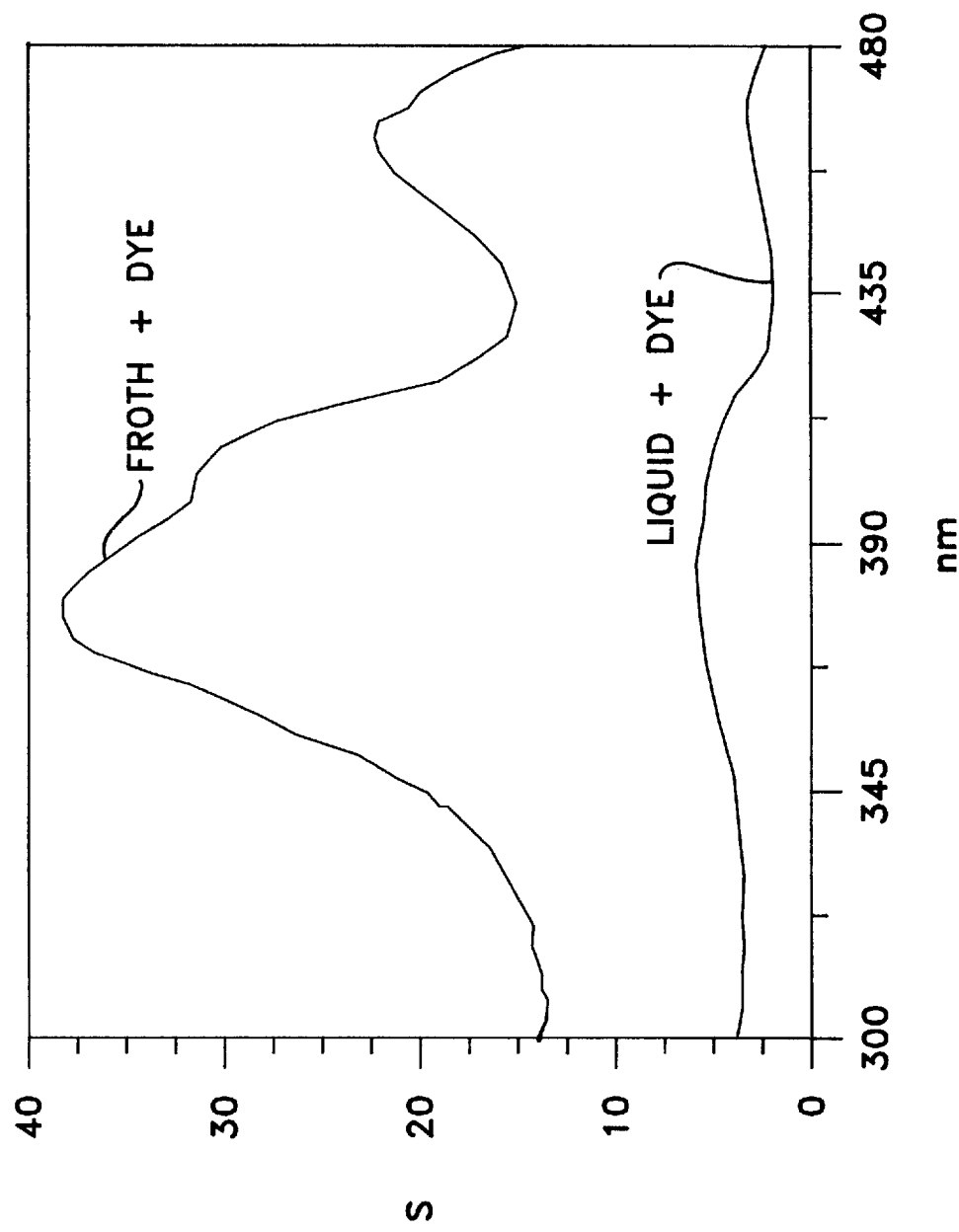
FIG. 5 shows a plot depicting an excitation spectra measured on a liquid blood/media/fluorescent dye mixture and on a blood culture froth above the same liquid mixture.
Figure 6:
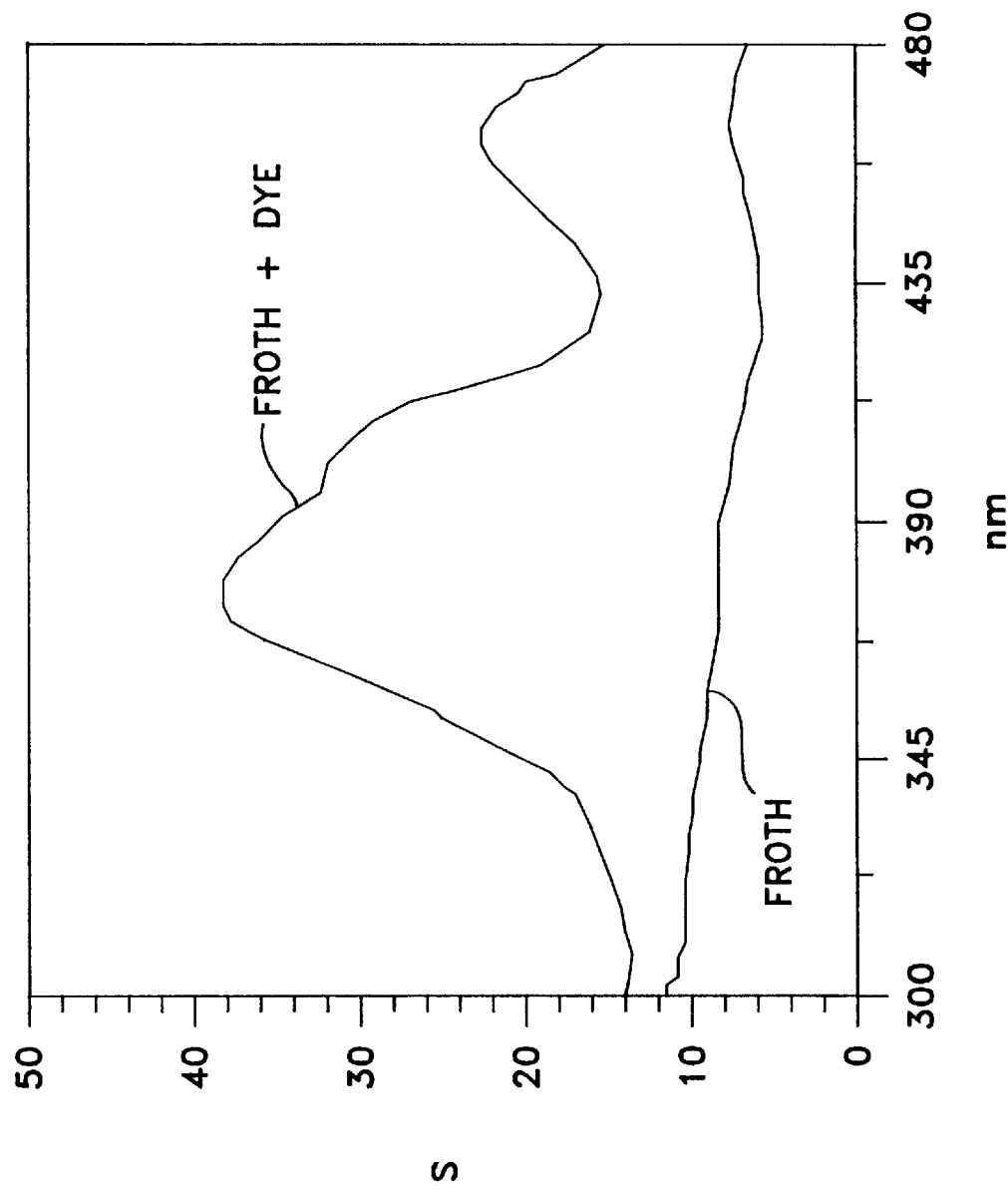
FIG. 6 shows a plot depicting an excitation spectra measured on a blood culture froth without a dye and on a blood culture froth with a fluorescent dye.

We will now discuss an application that involves a soluble fluorescent dye added to the blood/media mixture. FIG. 5 depicts an excitation spectra measured on a liquid blood/media mixture with a fluorescent dye added, and on a blood culture froth above the same liquid mixture. The fluorescence emission was measured using a narrow spectral window located at 520 nm. As can be seen, the spectrum intensity is again significantly higher for the froth, which reduces the effects of artifacts due to glass fluorescence. Another experimental result is shown in FIG. 6, depicting an excitation spectra measured on a blood culture froth without a dye, and on a blood culture froth with a fluorescent dye added. The effect of the added dye is clearly visible. In using such spectra, it is possible to improve the resolution capability by subtracting a typical fluorescence signal emitted by the froth alone.

The dye used in FIG. 6 was 8-hydroxypyrene-1,3,6-trisulfonic acid ("HPTS"), as sold by Molecular Probes, Eugene, Ore. This fluorescent dye shows a pH-dependent change in its excitation spectrum, and is commonly used as a ratiometric pH sensor. Again, the fluorescence emission was monitored at 520 nm.

Figure 7:
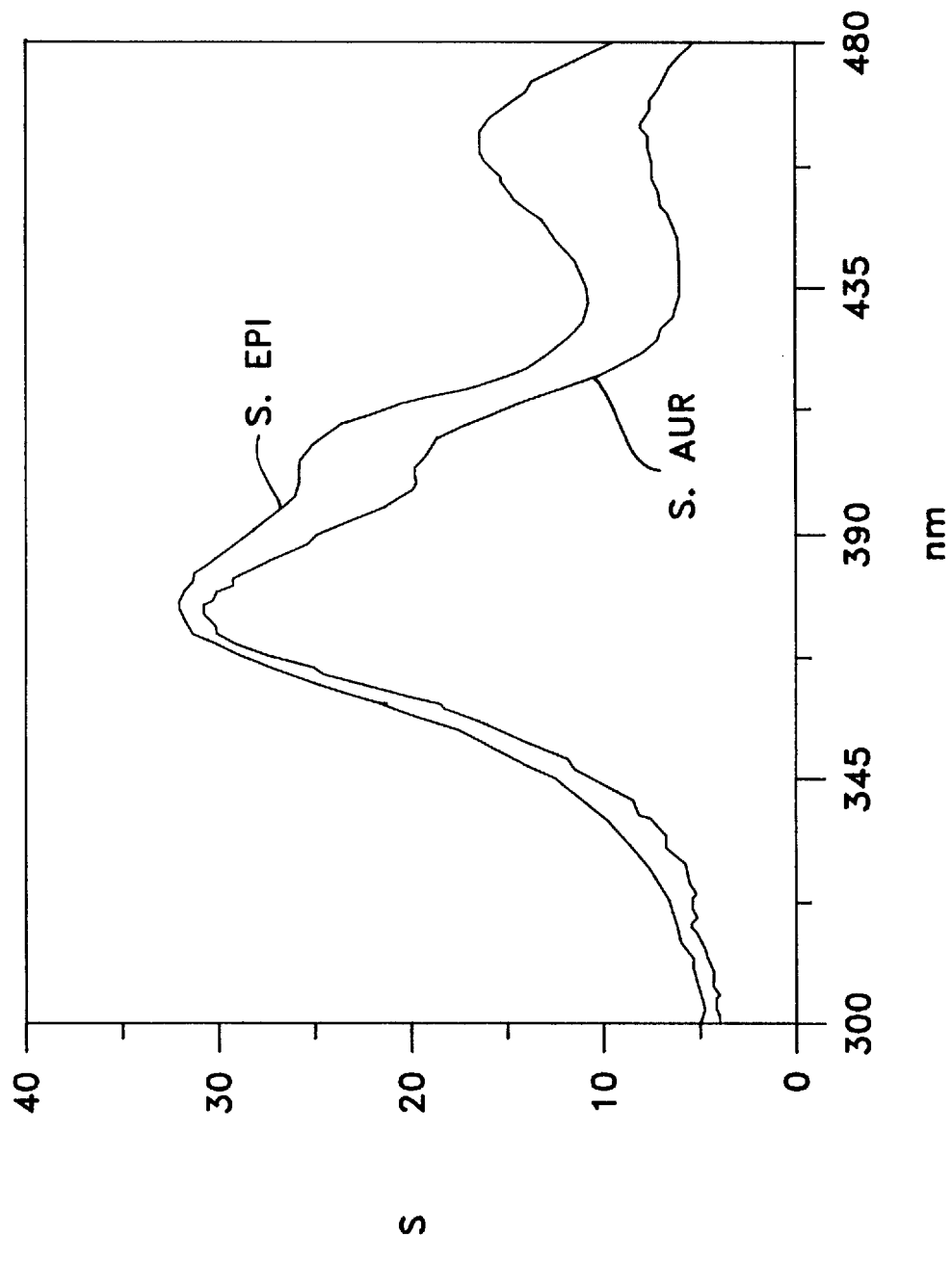
FIG. 7 shows a plot depicting an excitation spectra measured on a blood culture froth with a fluorescent dye for positive bottles containing S. epidermidis and S. aureus, respectively.

It is known that some species of bacteria, e.g., S. aureus, cause a change in pH within a blood culture. Other species, e.g., S. epidermidis, do not cause a pH change. Therefore, it should be possible to distinguish between S. epidermidis and S. aureus, which are clinically the most frequently observed species, by investigating the final pH-value in a blood culture bottle. FIG. 7 compares two excitation spectra, measured on blood culture froth with HPTS added. The two bottles are inoculated with S. epidermidis and S. aureus, respectively. The two spectra exhibit a clear difference in their peak heights, as shown in the following Table 1.

TABLE 1

| Organism | Peak Height Ratio 376 nm/462 nm |
|---|---|
| S. epidermidis | 1.91 |
| S. aureus | 4.07 |

FIG. 7 and Table 1 indicate that, in a culture bottle with HPTS added, a blood culture froth can be utilized to differentiate between S. epidermidis and S. aureus. If one only measured the excitation spectra of the liquid blood/media/IHPTS mixture no differentiation could be achieved because of the high absorption of the blood below 480 nm.

It would of course be within the spirit of the invention to use other fluorescent or colorimetric dyes that respond to different analytes such as $CO_2$, $O_2$, $NH_3$, $H_2S$, glucose, or others. In a variation of the invention, it is possible to supplement a common blood culture bottle containing a sensor disposed to the inner bottom, with a soluble sensor dye added to the culture media. In this case, one additional analyte can be monitored, which may allow for differentiating between more than two organism species.

A further variation of the invention is possible by adding a soluble fluorescent or colorimetric dye only to blood culture bottles that have become positive, using a known blood culture apparatus. Adding the dye can be accomplished without opening the blood culture bottle by means of a syringe. Since only about 10% of all inoculated bottles become positive, the extra workload required would be relatively low. By adding the dye, a differentiation between organism species can be achieved.

In still another variation of the invention, no soluble dye is added to a blood culture bottle containing a sensor disposed to the inner bottom, but a back-scattering spectrum from the blood culture froth is measured. The features of the back-scattering spectrum are dependent on the oxygen concentration within the bottle. Therefore, a chemical sensor at the bottom responding to, e.g., carbon dioxide could be combined with a froth measurement responding to oxygen.

Finally, it has to be emphasized that adding a soluble fluorescent dye to the blood/media mixture does not prevent one from measuring back-scattering spectra. This is so because the back-scattering intensity, which is measured at the excitation wavelength, is much higher than any fluorescence intensity measured at a longer wavelength. In other words, adding a soluble fluorescent dye to a blood culture bottle, generating a blood culture froth, and monitoring spectroscopic characteristics of the froth allows one to measure two additional analytes. If added to a bottle that already contains a chemical sensor at its inner bottom, three analytes can be measured overall.

What is claimed is:

1. A method of detecting bacteria in a blood culture bottle comprising the steps of:

providing a sealable blood culture bottle;

introducing a blood specimen and a growth medium into the sealable blood culture bottle to form a liquid mixture therein;

agitating the sealable blood culture bottle vigorously so that a froth is generated above the liquid mixture; and monitoring the froth to determine whether bacteria is present in the blood culture bottle by:

illuminating the froth with a light;

measuring a back-scattering intensity spectrum of the froth having a plurality of maxima; and determining whether bacteria is present in the blood culture bottle based upon a predetermined increase in said plurality of maxima.

2. A method according to claim 1, further comprising the step of introducing a soluble fluorescent sensor dye into the sealable blood culture bottle when forming said liquid mixture before the step of agitation.

3. A method according to claim 2, wherein said back-scattering intensity spectrum is a fluorescence emission spectrum generated by said fluorescent sensor dye in the froth.

4. An apparatus for detecting bacteria in a blood culture bottle comprising:

a sealable blood culture bottle having a liquid mixture comprising a blood specimen and a growth medium;

means for agitating the sealable blood culture bottle vigorously so that a froth is generated above the liquid mixture; and means for monitoring the froth to determine whether bacteria is present in the blood culture bottle including means for illuminating the froth with a light;

means for measuring a back-scattering intensity spectrum of the froth having a plurality of maxima;

means for determining whether bacteria is present in the blood culture bottle based upon a predetermined increase in said plurality of maxima.

5. An apparatus according to claim 4 wherein said sealable blood culture bottle further comprises a soluble fluorescent sensor dye in said liquid mixture.

6. An apparatus according to claim 5, wherein said back-scattering intensity spectrum is a fluorescence emission spectrum generated by said fluorescent sensor dye in the froth.

* * * * *